United States Patent [19]

Gorlovsky et al.

[11] 4,256,662
[45] Mar. 17, 1981

[54] PROCESS FOR PRODUCING UREA

[76] Inventors: David M. Gorlovsky, ulitsa Gagarina, 8, kv. 4, Dzerzhinsk Gorkovskoi oblasti; Vladimir I. Kucheryavy, prospekt Ilicha, 23, kv. 13, Gorky; Kapitolina N. Sineva, bulvar Zhdanova, 9/11, kv. 86; Vladimir V. Lebedev, prospekt Lenina, 85, kv. 6, both of Dzerzhinsk Gorkovskoi oblasti; Boris I. Pikhtovnikov, ulitsa Sovetskaya, 32, kv. 142, Vidnoe Moskovskoi oblasti; Jury A. Sergeev, prospekt Pobedy, 3, kv. 18, Dzerzhinsk Gorkovskoi oblasti; Yakov S. Teplitsky, ulitsa Osipenko, 3, kv. 16; Petr E. Korshunov, 2 mikroraion, 5, kv. 10, both of Chirchik Tashkentskoi oblasti; Sergei M. Simonov, prospekt Lenina, 85, kv. 27, Dzerzhinsk Gorkovskoi oblasti

[21] Appl. No.: 113,302

[22] Filed: Jan. 18, 1980

[51] Int. Cl.³ .......................................... C07C 126/00
[52] U.S. Cl. ...................................................... 564/67
[58] Field of Search .................................. 260/555 A

[56] References Cited

U.S. PATENT DOCUMENTS 3,317,601  5/1967  Otsuka ........................... 260/555 A
3,922,222  11/1975 Van Moorsel .................. 260/555 A
4,053,507  10/1977 Inoue ............................... 260/555 A

FOREIGN PATENT DOCUMENTS 819030  8/1959  United Kingdom ............... 260/555 A

OTHER PUBLICATIONS

Chemical Abstracts, vol. 78 (1973), Nos. 3754v, 3755w.
Weyermuller et al., "Dutch Urea Process", Chemical Processing, 9/24/62, pp. 19-23.

Primary Examiner—Brian E. Hearn
Attorney, Agent, or Firm—Lackenbach, Lilling & Siegel

[57] ABSTRACT

Urea is synthesized from ammonia and carbon dioxide at increased pressure and elevated temperature. The unconverted starting components are separated and recycled to the synthesis stage and the resulting urea solution is vacuum thickened. The liquor vapor resulting from the vacuum-thickening is condensed under a pressure of from 0.04 to 0.90 ata by means of indirect cooling water, followed by contacting the uncondensed liquor vapor with an aqueous solution of the unconverted starting feed at a temperature of from 10° to 60° C. and pressure of from 1.5 to 18 ata for subsequent absorption condensation. The process according to the present invention makes it possible to reduce the rate of consumption of steam (per ton of urea) by 0.1–0.25 t/t and the rate of consumption of the cooling return water by 6 to 14 m³/t.

4 Claims, 3 Drawing Figures

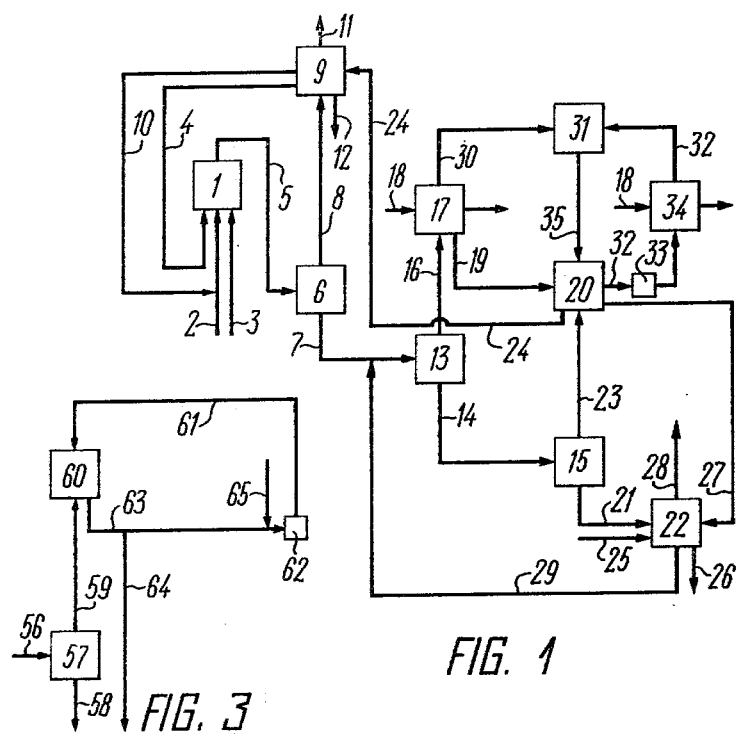
FIG. 1
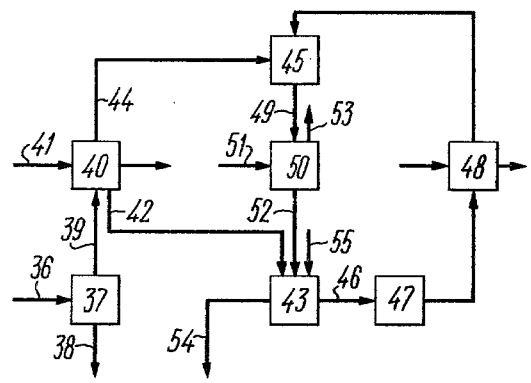
FIG. 3
FIG. 2

PROCESS FOR PRODUCING UREA

The present invention relates to the nitrogen industry of and, more particularly, to a process for producing urea.

FIELD OF THE INVENTION

The process according to the present invention is useful in the manufacture of nitrogen fertilizers for agriculture, as well as the production of protein additives for feedstuffs intended for ruminant animals. Furthermore, urea is employed in the synthesis of synthetic resins, preparation of adhesives, plastics, pharmaceutical somniferous agents, hygienic products (tooth pastes) and cosmetics (creams), as well as for the preparation of cyanuric acid and esters thereof, melamine, cyanates, hydrazine and certain types of dyestuffs.

BACKGROUND OF THE INVENTION

Known in the art are more than 50 principally different ways for the production of urea, though in commercial processes for the production of urea the following reaction is mainly used:

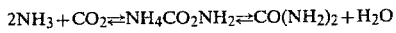

$$2NH_3 + CO_2 \rightleftharpoons NH_4CO_2NH_2 \rightleftharpoons CO(NH_2)_2 + H_2O$$

The processes enjoying the most extensive application in the production of urea throughout the world are exemplified by the "Stamicarbon" process (Holland) and the "Mitsui Toatsu" process (Japan).

In the "Stamicarbon" process (cf. French Patent No. 1,184,991; British Patent No. 819,030 or "Nitrogen", 1959, May No. 2, pp. 25-27; Chemical Processing, 1962, v. 25, No. 16 pp. 19-23), liquid ammonia is fed through a pre-heating unit and carbon dioxide, by means of a compressor to a unit for the synthesis of urea. A recycled solution of carbon-ammonium salts (CAS) is pumped into the same unit, the molar ratio between the components in the starting reaction mixture being $NH_3:CO_2:H_2O = 4.5:1:0.5$. The temperature in the mixer is 175° C., in the synthesis column—190° C.; the pressure in the synthesis unit is 200 ata.

The melt from the synthesis column containing 35-38% of $NH_3$, 10-12% of $CO_2$, 28 to 35% of $CO(NH_2)_2$ and 19-23% of $H_2O$ is throttled to 18 ata and delivered to the first step distillation unit consisting of a rectification column, preheater and a separator. In this unit the principal portion (about 90%) of the unreacted ammonia and carbon dioxide is separated from the solution of urea due to reduction of pressure from 200 to 18 ata and heating of the melt to 163° C.

The gases from the first step distillation are fed at a temperature of 120°-125° C. to a washing column, whereinto a solution of CAS is also fed from the second step distillation along with ammonia liquor and liquid ammonia. In this column condensation of water vapor occurs at 92°-96° C. and adsorption of the major amount of carbon dioxide from the distillation gases with the formation of a recycled solution of CAS containing 38 to 45% $NH_3$, 30 to 37% $CO_2$ and 22-27% $H_2O$. The ammonia vapor purified from carbon dioxide is fed to a condenser, wherefrom a portion of liquid ammonia is fed to spraying in the washing column, while the remaining ammonia is recycled to the synthesis.

The condensed ammonia along with the gases inert to the synthesis of urea is fed to a scrubber sprayed by the liquor steam condensate. The ammonia liquor produced here is used for spraying the washing column and the gas is throttled to atmospheric pressure and vented to the atmosphere through the tailing absorber.

After the first step distillation the synthesis-melt of urea containing 8-11% of $NH_3$, 1.5 to 2.5% of $CO_2$, 55-60% of $CO(NH_2)_2$, 28-35% of $H_2O$ is throttled to a pressure of 2.5-4.0 ata and passed to the second step distillation unit consisting of a rectification column, preheater and a separator.

In this unit the remaining portion of ammonia and carbon dioxide is distilled from the melt at 140°-142° C. The gases resulting from this second step distillation are fed to a condenser-absorber sprayed by the liquor vapor condensate. Here a solution of CAS is formed containing 33-50% $NH_3$, 10-16% $CO_2$, 35-55% $H_2O$. This solution is then pumped to the washing column.

The unabsorbed gases from the second step distillation unit are fed to an absorber sprayed by the liquor vapor condensate and a solution of ammonia and carbon dioxide circulated through the cooler. Other ammonia-containing gas streams are also fed to this absorber. The absorption heat is removed by means of a cooler. A portion of a weak solution of CAS formed in the absorber is continuously removed through a boiler to a desorber, whereinto live steam is also fed. The temperature in the bottom section of the desorber is maintained at 135°-145° C., pressure is 3 to 4 ata. The gas stream from the desorber (containing 45-60% $NH_3$, 5-10% $CO_2$ and 35-45% $H_2O$) is fed to the second step distillation condenser-absorber. The cooled water after the desorber is drained to a sewage system.

After the second step distillation the solution (containing 0.8-2.0% $NH_3$, 0.2-0.5% $CO_2$, 64-72% $CO(NH_2)_2$, 26-36% $H_2O$) is throttled to a residual pressure of 300 mm Hg and fed into a vacuum evaporator for pre-evaporation. In this apparatus the solution temperature is reduced, due to partial evaporation of water, to 95° C., while the content of urea is incrased to 74%. Then a two-step evaporation of the solution is effected. In the first step, the solution is evaporated to 93-95% under a residual pressure of 300 mm Hg and the temperature of 125° C.; in a second step the residual pressure is 20-50 mm Hg and temperature 138° C., whereby the content of urea is increased to 99.7-99.8%. Vacuum is ensured, as a rule, by means of a system of condensers and steam-ejection pumps. The liquor vapor condensate is treated in the above-described system of absorption-desorption.

The melt of urea after evaporation is dispersed into drops and atomized in a granulation tower. Cooling of the resulting granules is effected by air sucked through the granulation tower by ventilators. The granulated product is passed through a classifier (sifter), wherein the nonstandard granules are screened-off, then fed to a dissolving apparatus, wherefrom the resulting solution of urea is delivered to the evaporation stage. The commercial product is delivered to storage or to a consumer.

One of the most essential disadvantages of this prior art process resides in the necessity of using steam at a pressure of about 10 ata as a power stream in vacuum-ejection units, as well as cooling water necessary for its condensation. Furthermore, it should be also noted that a portion of the vapor-gas stream remaining uncondensed after completion of the liquor vapor condensation due to an indirect heat-exchange with the cooling return water contains impurities of ammonia, carbon dioxide and urea which may be present in the gas phase both as vapors and as mist. This vapour-gas mixture is then contacted with the power steam-working stream in an ejector intended for ensuring vacuum in the zone of thicknening of the urea solution. As a result, there contamination of the power steam with ammonia, carbon dioxide and urea occurs. The power steam condensate containing these impurities is added to the liquor vapor condensate and then subjected to separation to purified waste waters removed from the system and a stream of ammonia, carbon dioxide and urea recycled to the process. Due to the power steam condensate the amount of waste waters is increased by 20 to 50%. It is clear that the greater the amount of waste water, the greater the load and rates of power consumption at the purification stage.

Also known in the art is a process for the production of urea belonging to "Mitsui Toatsu", a Japanese company. (Cf. U.S. Pat. No. 3,317,601, British Patent No. 1,047,954, FRG Patent No. 1,299,295 and French Patent No. 1,381,931). This process comprises feeding, into a reactor, gaseous carbon dioxide, liquid ammonia and a recycled solution of CAS and urea. The molar ratio between the components in the starting reaction mixture $NH_3:CO_2:H_2O=(3.7-4.5):1:0.4$. The synthesis is conducted under a pressure of from 220 to 230 atm and at a temperature within the range of from 180° to 195° C. The temperature control in the reactor is effected by heating of ammonia. The degree of conversion of carbon dioxide to urea amounts to 50-67%.

The synthesis melt of urea from the reactor is fed to a three stage distillation. In the first stage the operation pressure of 18 ata and temperature of 155° C. are maintained, at the second stage—pressure 3 ata and temperature 130°, at the third stage pressure is 0.3 ata and temperature is 115° C. The gases from the first stage distillation are admitted to a high-pressure absorber, wherein the formation of a recycled solution of CAS and washing of ammonia vapors from contaminating carbon dioxide are effected. Ammonia is further condensed and a portion thereof is used to spray the absorber, while the major amount of ammonia is recycled to the synthesis. Temperature conditions in the absorber (100° C. in the bottom section and 50° C. in the top section) are ensured by means of a heat-exchanger through which a solution from the vacuum crystallyzer is recycled and due to the supply, to spraying in the absorber, of liquid ammonia and ammonium liquor resulting from washing of the inert gases remaining after condensation of ammonia.

The gases from the second stage of distillation are fed to a low-pressure absorber, wherein water vapors are condensed at a temperature of 50° C. and ammonia and carbon dioxide are absorbed with the formation of a solution of CAS and urea which are then fed to spraying of the high-pressure absorber. The gases from the third stage distillation are washed with the mother liquor obtained after separation of urea crystals in a centrifuge, in a cooler-absorber, wherefrom the solution of CAS and urea is fed to spraying of the low-pressure absorber.

After the third stage of distillation the solution containing 70% urea is fed to a vacuum-crystallizer, wherein evaporation of the solution and crystallization of urea are effected under a residual pressure of 60-70 mm Hg and temperature of about 60° C. The slurry is thickened in a decanter and; the clarified mother liquor is recycled to the vacuum crystallizer by means of a pump through the heat-exchanger of the high-pressure absorber. Vacuum in the crystallization unit is maintained by means of a system of condensers and steam-ejector units.

Urea crystals are partly dehydrated in a centrifuge, dried to a moisture content of 0.2-0.3% and fed to a melting unit positioned over the granulation tower. The molten urea is pulverized across the tower, wherein the granules are air-cooled first to 80°-90° C. and then to a lower temperature in the bottom section of the tower. The granulate is screened and the final product is delivered to storage.

An embodiment of the process for producing urea according to patents to "Mitsui Toatsu" (cf. FRG Patent No. 1,668,856, 1973; French Patent No. 2,099,882, 1972) resides in that said vacuum thickening of the solution of urea is conducted in two steps, namely: by evaporation and crystallization at a temperature below the melting point of urea to form a slurry, where from the residual moisture is removed by heating at a temperature above the melting point.

In order to create a vacuum at the stage of thickening of the solution of urea in both embodiments of the above-discussed process of "Mitsui Toatsu", as well in the "Stamicarbon" process, a system of condensers and steam-ejection units is required, the "Mitsui Toatsu" process possesses the same disadvantages which were mentioned above as characteristic of the "Stamicarbon" process.

It is an object of the present invention to overcome the above-mentioned disadvantages.

It is an object of the present invention to provide a simpler process for the production of urea which would make it possible to lower power consumption.

The object of the present invention is accomplished in a process for producing urea which comprises:
(a) synthesis of urea from ammonia and carbon dioxide under a pressure of from 140 to 400 ata and at a temperature within the range of from 160° to 230° C.;
(b) separation of the resulting aqueous solution of urea from the ammonia and carbon dioxide not converted to the desired product;
(c) separation of liquid or gaseous streams of ammonia and carbon dioxide from the gases which are inert with respect to the synthesis of urea and purified waste water withdrawn from the process;
(d) recirculation of said liquid or gaseous streams of ammonia and carbon dioxide to the stage of the synthesis of the desired product;
(e) vacuum-thickening the resulting solution of urea under a pressure of from 0.04 to 0.90 ata with the recovery of dehydrated urea in the condensed phase and a mixture of water, ammonia and carbon dioxide in the vapor phase;
(f) converting the dehydrated urea into solid particles and cooling in a current of air;
(g) water washing urea dust from the air from the stage of converting the dehydrated urea into solid particles and their cooling to give an aqueous solution of urea recycled to said stage of vacuum thickening;
(h) condensation of the mixture of water, ammonia, carbon dioxide and urea from the vapor phase resulting from the stage of vacuum thickening due to its indirect cooling with the formation of a liquor vapor condensate;
(i) supplying the condensate of the liquor vapor to the stage of recovery to gases inert with respect of the synthesis of urea and purified waste water;

(j) supplying ammonia and carbon dioxide contained in the uncondensed portion of the vapor phase from the stage of vacuum thickening after said indirect cooling to the stage of separation of the gases inert with respect to the synthesis of urea and purified waste water, wherein in accordance with the present invention the non-condensed portion of the vapor phase from the stage of vacuum thickening after said indirect cooling is subjected to absorption condensation under a pressure at which said vapor phase is delivered to the stage of absorption-condensation, said absorption-condensation being effected by way of direct contact of said vapor phase with a cooling agent-absorbent having a temperature within the range of from 10° to 60° C., pressure of from 1.5 to 18 ata and containing dissolved in water 0.2 to 3.4% by weight of ammonia, 0 to 1.0% by weight of carbon dioxide and 0 to 50% by weight of urea, whereafter at least a portion of the resulting solution is fed to the stage of separation of the gases inert with respect to the synthesis of urea and purified waste water or to the stage of separating of the aqueous solution of urea from the ammonia and carbon dioxide not converted to the desired product, or to the stage of vacuum thickening of the solution of urea.

An embodiment of the process according to the present invention is that said adsorption-condensation is effected using said liquor vapor condensate as a cooling agent-absorbent.

Another embodiment of the present invention is that as the cooling agent-absorbent, use is made of waste waters purified from contaminating urea under a pressure of from 16 to 18 ata in the stage of separation of the gases which are inert with respect to the synthesis of urea and purified waste water.

Still another embodiment of the process according to the present invention is that as the cooling agent-absorbent, use is made of a solution of urea resulting from water washing of urea dust from the air from the stage of converting the dehydrated urea into solid particles and cooling, and/or a solution of urea resulting from separating of the aqueous solution of urea from the ammonia and carbon dioxide not converted to the desired product.

The process according to the present invention makes it possible to avoid supplying power steam to the zone of contacting with the vapor-gas stream remaining after completion of the liquor vapor condensation due to an indirect cooling. As a result, the rate of consumption of steam and return water (necessary for steam condensation) is reduced. Furthermore, owing to contacting, in the absorber-condenser, of the vapor-gas stream (remaining after completion of the liquor vapour condensation by indirect cooling) with the aqueous absorbent (for example, with the cooled liquor vapor condensate) there occurs a substantially complete absorption-condensation of ammonia, carbon dioxide and urea contained in said vapor-gas stream. In doing so, in contrast to the prior art processes, as a result of recuperation of said impurities there is no any additional formation of waste waters; i.e. the total amount of waste waters from the plant of urea production is reduced. Due to the lowered amount of waste waters, the power consumption for their treatment is reduced, the degree of purification is increased along with reduced losses of the starting materials and the desired product.

Vacuum in the zone of thickening of the solution of urea is maintained, according to the present invention, by absorption-condensation of the vapor-gas stream remaining after completion of the liquor vapor condensation by an indirect cooling upon contacting with the aqueous absorbent, as well as due to utilization of the potential energy of the aqueous absorbent stream taken-off at the point of the process flowsheet, where the pressure of this stream is above atmospheric. When it is required to increase the pressure of the aqueous absorbent stream by 2-3 ata by means of a pump (taking into account the fact that liquids are substantially non-compressible media), the electric power consumption (for operation of the pump motor) is rather low and costs of electric power are generally smaller than those of steam.

The practical application of the process according to the present invention eventually makes it possible to lower the steam consumption rate (per ton of urea) by 0.1-0.25 ton/ton and the consumption rate of return water-by 6-14 m³/ton.

BRIEF DESCRIPTION OF THE DRAWINGS

Further objects and advantages of the present invention will now become more fully apparent from the following detailed description of the process for producing urea, specific illustrative examples and drawings, wherein:

FIG. 1 shows a principal flow-sheet of the first embodiment of the process for producing urea according to the present invention;

FIG. 2 shows a principal flow-sheet of the second embodiment of the process for producing urea according to the present invention;

FIG. 3 shows a principal flow-sheet of the third embodiment of the process for producing urea according to the present invention.

The process according to the present invention stipulates, the production of urea from ammonia and carbon dioxide.

To the unit of synthesis of urea 1 (FIG. 1) the starting component streams are fed via line 2 (ammonia) and line 3 (carbon dioxide), while via line 4 there is supplied a recycled stream of the ammonia and/or carbon dioxide not converted to the commercial product, contaminated with water or urea. The synthesis of urea is conducted at a temperature of from 160° to 230° C. under a pressure ranging from 140 to 400 ata, and at molar ratios of the components in the starting reaction mixture: $NH_3:CO_2=2.5$ to 6.0 and $H_2O:CO_2=0$ to 1.2. Under these conditions the degree of conversion of carbon dioxide to urea amounts to 40-80%.

From the synthesis unit the reaction mixture consisting of ammonia, carbon dioxide, urea and water is delivered, via line 5, to the treatment in unit 6, wherefrom the separated aqueous solution of urea is withdrawn via line 7 (with a concentration of 60-75%) and the ammonia and carbon dioxide not converted to the desired product with a small amount of water are withdrawn via line 8. To ensure such separation of the components in the unit 6, the reaction mixture is subjected to distillation at a temperature within the range of from 110° to 180° C. and a step-wise reduction of pressure from the value maintained in the unit of synthesis of urea 1 to the value approaching atmospheric pressure. The last step of distillation which is frequently performed in vacuum is substantially the stage of pre-evaporation. As a result, the ammonia and carbon dioxide not converted to urea become substantially completely converted to the gas phase. These gas streams are referred to as distillation gases.

The distillation gases containing ammonia, carbon dioxide and water are delivered via the line 8 to the processing, by conventional techniques, to unit 9 in order to precondition them for a repeated use in the unit of synthesis of urea 1. Depending on the scheme of processing the distillation gases, the prior art processes are classified broadly into two groups: with the liquid recycle and with gas recycle.

In the case of liquid recycle the gases resulting from the last step of distillation are subjected to aqueous absorption and condensation to give a diluted solution of carbon-ammonium salts (CAS). Then this solution of CAS is used for absorption of gases from the preceding distillation step effected under a higher pressure, and so on. This stage of the process is completed by the absorption-condensation of the gases of the first step distillation, whereby a recycled CAS solution is obtained which is delivered to the unit 1 via the line 4. In certain cases, a portion of ammonia contained in the distillation gases is washed to remove contaminating carbon dioxide. It is then water condensed and recycled, via the line 10 to the synthesis unit in the pure liquid form.

In the process schemes with gas recycle, ammonia and carbon dioxide contained in the distillation gases are separated by means of selective absorbents and the resulting streams of pure ammonia and carbon dioxide are separately recycled to the synthesis unit.

In the unit 9 water washing is effected to purify the gases which are inert with respect to the synthesis of urea (nitrogen, hydrogen, methane, carbon monoxide, oxygen and the like) from contaminating ammonia and carbon dioxide. These inert gases are inevitably involved in the process cycle mixed with the starting reagents. These gases, after washing off the contaminating ammonia and carbon dioxide, are exhausted to the atmosphere via the line 11 or utilized in related production processes.

In addition, the unit 9 purifies certain liquid streams from contaminating ammonia, carbon dioxide and urea. These products are recycled to the production process, while the purified waste water is removed via the line 12 (this is discussed in more detail hereinafter).

The aqueous solution of urea from the unit 6 is delivered via the line 7 to the first step of vacuum-evaporation in unit 13, wherein the solution is evaporated to a urea concentration of 93–96% at a temperature of 125° C. under a residual pressure of from 300 to 360 mm Hg. This solution is further passed, via the line 14, to the second step of evaporation in unit 15, while liquor vapors (water vapor with ammonia, carbon dioxide and urea) are delivered, via the line 16, to the condenser 17 cooled by return water supplied via the line 18. In said apparatus 17 the major portion of the liquor vapor fed via the line 16 is condensed; the resulting liquor vapor condensate is delivered via the line 19 to a unit 20 for collection of this condensate.

In the second step of evaporation (in the unit 15) the solution of urea is evaporated to a concentration of 99.6–99.8% at a temperature of 135°–140° C. under a residual pressure of from 30 to 50 mm Hg. The resulting urea melt is passed via the line 21 to the unit 22 for granulation and cooling of the final product. The liquor vapor separated in the unit 15 is condensed and the thus-obtained condensate of the liquor vapor is delivered to the collecting unit 20 for the condensate via the line 23.

From the unit 20 the liquid stream (a weak aqueous solution of ammonia, carbon dioxide and urea) is delivered via the line 24 to the treatment (by conventional technique) to the unit 9. Therewith, a portion of this stream passing via the line 24 is used for absorption of the distillation gases from the second and/or the third step. Another portion of the stream passing along the line 24 is used for absorption of ammonia and carbon dioxide from the exhaust and off-gases to give a weak solution of CAS. Ammonia and carbon dioxide are recovered from this solution by desorption at a temperature of from 130° to 135° C. under a pressure of 3 ata and then combined with the stream of the distillation gases from the second step. The solution remaining after the description is separated, by a special treatment at a temperature of 180°–200° C. under a pressure of from 16 to 18 ata, from contaminating urea and then, the residual amounts of ammonia and carbon dioxide are desorbed from this solution at a temperature of 115° C. under atmospheric pressure. The waste waters thus-purified from contaminating ammonia, carbon dioxide and urea are withdrawn from the system via the line 12.

A current of atmospheric air is supplied to the unit 22 via the line 25 to remove the crystallization heat of urea and lower granule temperature from the solidification point to the required value (50°–60° C.). The granulated commercial product, after separation of the nonstandard granules by means of a sifter, is delivered to storage via the line 26 or supplied to consumers. The spent air contaminated with urea dust is washed by an aqueous absorbent (such as liquor vapor condensate) supplied to the unit 22 via the line 27. The purified air stream is vented via the line 28 to the atmosphere, while the aqueous solution of urea obtained after washing off the urea dust is used for the dissolution of said nonstandard granules and then delivered via the line 29 to the unit 13 for the recovery of urea from the solution in the solid commercial form.

In one embodiment of the process according to the present invention the non-condensed portion of the liquor vapor from the unit 17 is delivered via the line 30 to an absorber-condenser 31, wherein the absorption-condensation of the stream passed via the line 30 is effected thus maintaining in the liquir vapor condenser 17 a residual pressure of from 280 to 300 mm Hg. As the absorbent, use is made of the stream passed via the line 32 from the collection unit 20 for the liquor vapor condensate. The stream delivered via said line 32 is preliminarily compressed to a pressure of 2–4 ata by means of a pump 33 and then cooled in a cooler 34 to a temperature of from 20° to 40° C. The weak aqueous solution of ammonia, carbon dioxide an urea withdrawn from the apparatus 31 via the line 35 is then delivered to the unit 20.

Another embodiment of the present invention differs from the above-described one merely in that into the absorber-condenser 31, there is fed as the absorbent, a cooled liquid stream from the stage of purification of waste waters in the unit 9 under a pressure of 16–18 ata to remove contaminating urea (for example, by way of heat-treatment at a temperature ranging from 180° to 200° C.). The mixed stream from the absorber-condenser 31 is passed to the system of treatment of waste waters (unit 9).

One of the principal disadvantages of using steam-ejection units for thickening urea solutions is due to the fact that to complete the condensation of liquor vapors, the pressure of the latter is increased by means of power steam. In view of this fact we have studied the possibility of elimination, from the process scheme, of said steam-ejection units. To do this, we sought for the method of a maximum (or substantially total) condensation in vacuum of that portion of the liquor vapor which remains noncondensed after the indirect cooling in the condenser by return water. The method of direct absorption-condensation of liquor vapors in a mixing type condenser appeared more advisable.

The supply of pure water (or steam condensate) to said mixing condenser (hereinafter referred to as absorber-condenser) was unsuitable, since it would have resulted in an increased amount of waste waters and, consequently, higher power energy consumption at the stage of purification of these waste waters. Not suitable was the use, as the absorbent, of any substances taking no part in the process for producing urea; otherwise, the stage of separation of ammonia, carbon dioxide and urea contained in the liquor vapor from the mixture with the absorbent would have been necessary, thus entailing more energy to be consumed. All these considerations have led to the idea of using certain streams from the unit of synthesis of urea, in particular the liquor vapor condensate, as an agent for the absorption-condensation of the uncondensed portion of the liquor vapor.

However, due to the presence of volatile components—ammonia and carbon dioxide—in these absorbents, providing the required vacuum at the supply of liquid streams from the unit of synthesis of urea for contacting with the noncondensed portion of the liquor vapors looked unrealizable. Nevertheless, we have decided to carry out experiments and found unexpectedly that it is actually possible to retain the required vacuum at the supply of aqueous solutions of ammonia, carbon dioxide and urea from the urea synthesis unit to the absorber-condenser, provided that the temperature and pressure of the absorbent, as well as its composition are to be controlled within the specified range.

According to the data obtained from said experiments, the following characteristics of the absorbent are recommended: pressure from 1.5–2 to 17–18 ata; the temperature of from 10° to 60° C.; the content of ammonia from 0.4 to 4.0% by weight; the content of carbon dioxide of from 0 to 1% by weight; that of urea—from 0 to 50% by weight.

The upper limit of the absorbent pressure is selected so as to avoid unrational complication of the process and increased power consumption required of compressing the absorbent above 18–20 ata prior to supplying thereof to the absorber-condenser 31.

The lower limit of the temperature range is selected in order to preclude the risk of crystallization of the absorbent and to facilitate attaining the selected low temperatures. The upper limit is selected because at a temperature of above 60°–70° C. it is impossible to completely condense the liquor vapors in vacuum.

The ranges of concentration of the components in the solution intended for the use as the absorbent are selected to ensure the required vacuum in the zone of absorption-condensation of the liquor vapor.

Supplied to the absorber-condenser 31 as the absorbent can be any liquid streams from the unit of urea production or related units, or mixtures of the streams, provided that the above-specified requirements relative to the operating temperatures, pressures and absorbent composition are obeyed.

Still another embodiment of the process according to the present invention resides in that after the second stage of distillation the synthesis melt of urea is supplied via the line 36 (FIG. 2) to the pre-evaporation unit 37, wherein the temperature is maintained at 88° C. and the residual pressure at 369 mm Hg. From the stage of pre-evaporation the solution of urea is delivered via the line 38 to the subsequent stage of the process, while the vapor-gas mixture is fed via the line 39 to the pre-evaporation condenser 40 cooled by return water supplied via the line 41. In this unit, a condensate of the liquor vapor is obtained at a temperature of 66° C. under a residual pressure of 348 mm Hg. The condensate is drained to the collector 43 via the line 42. The uncondensed portion of the liquor vapors from the unit 40 is delivered via the line 44 to the absorber-condenser 45, wherein as the absorbent use is made of the weak aqueous CAS and urea solution recycled from the collector 43 via the line 46. This solution is precompressed by means of a pump 47 to 3–4 ata and cooled with return water to 25°–35° C. in a cooler 48. From the absorber-condenser 45 the mixed stream at the temperature of 37°–38° C. is fed via the line 49 to spraying of the absorber 50 which is intended for absorption of ammonia from the stream of the off- and exhaust gases supplied via the line 51 under a pressure close to atmospheric. The solution obtained in the absorber 50 having a temperature of 40°–42° C. is drained to the recycle collector 43 the via line 52, while the purified gas stream is fed via the line 53 to the off-gas collector (not shown).

To maintain a constant composition of the recycled solution between the units 43 and 50, a portion of the liquid from the collector 43 is fed via the line 54 to the unit for purification of waste waters, while into the collector 43 there is simultaneously added the liquor vapor condensate via the line 55 from the first and second stage evaporation units.

A further embodiment of the present invention consists in that the liquor vapors from one of the stages of vacuum thickening (pre-evaporation, evaporation of the first or second step, vacuum crystallization) are fed via the line 56 (FIG. 3) to a condenser 57, wherein the liquor vapor condensate is formed. The resulting liquor vapor condensate is drained via the line 58 to a collector (not shown), and then treated in the unit of purification of waste waters. The uncondensed portion of the liquor vapors is delivered via the line 59 to an absorber-condenser 60, wherein as the absorbent use is made of the aqueous solution of urea with a concentration of from 20 to 50% and at a temperature of from 10° to 60° C. This solution is fed via the line 61 and compressed by means of a pump 62 to a pressure of from 4 to 10 ata. A portion of the mixed stream supplied via the line 63 from the absorber-condenser 60 is delivered via the line 64 to treatment in a distillation unit (not shown). The other portion of the stream is recycled via the line 61 by means of the pump 62 through the absorber-condenser 60. To ensure a constant concentration of the recycled stream supplied via the line 61, the stream is replenished by the urea solution fed via the line 65 from, for example, the unit 22 (FIG. 1) for air cleaning from urea dust, from the dissolution vessel for non-standard granules, and the like.

EXAMPLE 1

Fed into the unit 1 of the synthesis of urea (FIG. 1) are supplied 1,600 kg/hr of liquid ammonia with contaminating water in the amount of 3.33 kg/hr, carbon dioxide gas in the amount of 745 kg/hr; water—0.4 kg/hr, inert gases—15.4 kg/hr and a recycled CAS solution containing ammonia—503.3 kg/hr, carbon dioxide—459.6 kg/hr, water—268.2 kg/hr, urea—0.17 kg/hr. The process in the reactor for synthesis of urea is conducted under a pressure of 200 ata and a temperature of 190° C.

The synthesis melt of urea containing ammonia in the amount of 1,526 kg/hr, carbon dioxde—460 kg/hr, water—580 kg/hr, urea—1.014 kg/hr, inert gases—15.4 kg/hr is delivered for processing to the unit 6, wherein a two-step distillation of the synthesis melt and a preliminary evaporation of the solution of urea is performed.

In the first step the distillation is conducted under a pressure of 18 ata and at a temperature of 160° C. Under these conditions from the synthesis melt there are distilled-off gases containing ammonia in the amount of 1,400 kg/hr, carbon dioxide 416 kg/hr, water 92.5 kg/hr, inert gases 15.4 kg/hr. The remaining synthesis melt (containing ammonia 126 kg/hr, carbon dioxide 44 kg/hr, water 487.5 kg/hr, urea 1,014 kg/hr) is delivered to the second step of distillation conducted under a pressure of 3 ata and at a temperature of 138° C. The separated stream of distillation gases of the second step contains ammonia 114.4 kg/hr, carbon dioxide 41.5 kg/hr, water 72.0 kg/hr. The synthesis melt remaining after the second step distillation (containing 11.6 kg/hr ammonia, carbon dioxide 2.5 kg/hr, water 415.5 kg/hr, urea 1,014 kg/hr) is introduced into the vacuum evaporator of the pre-evaporation unit, wherein the residual pressure is maintained at 300 mm Hg. Due to the auto-evaporation at the temperature of 95° C., passed into the vapor phase are ammonia (5.2 kg/hr) and water (71.0 kg/hr).

The liquid phase delivered from the unit 6 via the line 7 to the first step of vacuum evaporation in the unit 13 has the following composition: ammonia 6.4 kg/hr, carbon dioxide 2.5 kg/hr, water 344.5 kg/hr, urea 1.014 kg/hr.

The distillation gases from the first and second steps supplied via the line 8 are processed in the unit 9. In doing so, the second step distillation gases are fed to the absorber-condenser, wherein temperature is maintained at about 40° C. Also fed thereinto are the liquor vapor condensate containing ammonia 0.19 kg/hr, water 37.8 kg/hr, urea 0.07 kg/hr and the gas stream from the desorber containing ammonia 12.3 kg/hr, carbon dioxide 2.1 kg/hr, water 10.3 kg/hr. The desorber is one of the elements of the system of purification of waste waters in the unit 9. The solution of CAS produced in the condenser-absorber and containing ammonia 126.89 kg/hr, carbon dioxide 43.6 kg/hr, water 120.1 kg/hr, urea 0.07 kg/hr is used for spraying of the washing tower, whereinto there are also fed the gases from the first step distillation, ammonia liquor (water 55.6 kg/hr, ammonia 38.3 kg/hr, urea 0.1 kg/hr) from the absorber of ammonia washed out of the mixture with inert gases and liquid ammonia (1,410 kg/hr) from condensers of recycled ammonia. The resulting CAS solution formed at 95° C. in the washing tower (containing ammonia 503.3 kg/hr, carbon dioxide 459.6 kg/hr, water 268.2 kg/hr, urea 0.17 kg/hr) is then used in the synthesis reactor of the unit 1 and vapors of recycled ammonia purified from contaminating carbon dioxide and water (ammonia 2,471.89 kg/hr, inert gases 15.4 kg/hr) is fed to condensation. The resulting liquid ammonia (2,432.79 kg/hr) is partly employed for spraying of the washing tower and the remaining portion is recycled to the synthesis reactor via the line 10. The gas phase from the condensers of recycled ammonia (ammonia 39.1 kg/hr, inert gases 15.4 kg/hr) is introduced into the absorber of ammonia operating under a pressure equal to the pressure in the first step distillation unit. The liquor vapor condensate (ammonia 0.3 kg/hr, water 55.6 kg/hr, urea 0.1 kg/hr) is fed to spraying in the absorber. The solution obtained in the absorber of ammonia (ammonium liquor) is used for spraying of the washing tower. After washing-off of the main portion of ammonia, the uncondensed gases (ammonia 1.1 kg/hr, inert gases 15.4 kg/hr) are throttled to atmospheric pressure and vented to the atmosphere through the tailing absorber via the line 11.

Also fed into the first evaporation step (unit 13), in addition to the stream supplied via the line 7 with the composition specified hereinabove, is the stream containing water 42.0 kg/hr, urea 99.76 kg/hr, supplied via the line 29 and obtained by absorption of urea dust and dissolution of nonstandard granules. In the unit 13 the mixed stream passes through the vacuum evaporator, wherein temperature is maintained at 125° C. and the residual pressure is 300 mm Hg, and then through a separator. From the separator a liquid stream is withdrawn via the line 14 containing ammonia in the amount of 0.48 kg/hr, water 47.22 kg/hr, urea 1.112 kg/hr and this solution is delivered to the second step of evaporation (into the unit 15).

In the second step of evaporation the process is conducted at a temperature of 138° C. under a residual pressure of 35 mm Hg. The liquor vapors thus produced contain ammonia in the amount of 0.48 kg/hr, water 44.42 kg/hr, and urea 1.20 kg/hr. These vapors are condensed and supplied, via the line 23, to the collector 20 for the liquor vapor condensate. The urea melt containing water in the amount of 2.8 kg/hr, urea 1,110.8 kg/hr is discharged from the evaporation unit 15 and passed, via the line 21, to the granulation unit 22. The melt is sprinkled in the granulation tower, whereinto cooling air is fed via the line 25. The resulting cooled granules are screened on a sifter, whereon aggregates and large-size granules are separated to be dissolved afterwards. The air stream is washed with the aqueous absorbent supplied via the line 27 (purified waste water or liquor vapour condensate) to remove urea dust and vented to the atmosphere via the line 23. The final product containing 1,000 kg/hr of urea, water 2.6 kg/hr is discharged via the line 26 to storage or to consumers while the solution obtained by dissolution of large-size granules and absorption of urea dust is delivered to treatment in the unit 13 via the line 29, The vapor-gas mixture containing ammonia in the amount of 5.92 kg/hr, carbon dioxide in the amount of 2.5 kg/hr, water 339.28 kg/hr, urea 1.76 kg/hr is introduced into the condenser 17 cooled by return water supplied via the line 18. In this condenser a condensate of the liquor vapor is obtained at a temperature of 74° C. and under a residual pressure of 280 mm Hg. This liquor vapor condensate containing 5.12 kg/hr of ammonia and carbon dioxide 2.5 kg/hr, water 329.28 kg/hr and urea in the amount of 1.66 kg/hr is drained via the line 19 to the unit 20 for collection of the liquor vapor condensate. From the unit 20 a portion of the liquor vapor condensate is fed to the unit 9 via the line 24, wherein ammonia is isolated from said condensate along with carbon dioxide and urea in order to recycle these components to the production process, while the purified waste water is withdrawn from the system via the line 12.

In accordance with the present invention, the uncondensed portion of the liquor vapor containing ammonia in the amount of 0.8 kg/hr, water 10 kg/hr, urea 0.1 kg/hr is fed from the unit 17 via the line 30 to the absorber-condenser 31, whereinto is also fed via the line 32 the unpurified waste waters from the recycle collector mounted in the unit 20. These waste waters compressed by the pump 33 to a pressure of 6 ata cooled to a temperature not exceeding 60° C. in the cooler 34 contain ammonia in the amount of 47 kg/hr, carbon dioxide in the amount of 15 kg/hr, water 2,430 kg/hr, urea 9 kg/hr.

The mixed stream from the absorber-condenser 31 is again recycled to the unit 20 via the line 35.

Owing to the process according to the present invention the rate of steam consumption per ton of urea is reduced by 0.15 ton, while the rate of consumption of cooling water (calculated also per ton of urea) is reduced by 9 m$^3$/ton.

EXAMPLE 2

The process is performed under conditions similar to those described in Example 1, except that a stream of waste waters cooled to a temperature of 40° C. after a heat-treatment or any other treatment (for the purpose of the removal of contaminating urea) carried out under a pressure of 18 ata is fed from the unit 9 to the absorber-condenser 31. This stream contains 10 kg/hr of ammonia, 4 kg/hr of carbon dioxide and 390 kg/hr of water. The mixed stream from the absorber-condenser 31 is delivered to the system of processing of waste waters (into the unit 9).

All other parameters of the process, as well as the effect obtained are similar to those described in the foregoing Example 1.

EXAMPLE 3

The process is carried out under conditions similar to those described in Example 1. However, the solution passing after the second step distillation from the unit 15 and containing 346 kg/hr of ammonia, 136 kg/hr of carbon dioxide, 14,614 kg/hr of water, 26,376 kg/hr of urea is fed via the line 36 (FIG. 2) to the vacuum-evaporator of the pre-evaporation unit 37, wherein temperature is 88° C. and the residual pressure is 369 mm Hg. After separation of phases in the separator, the liquid stream is withdrawn via the line 38. This liquid stream contains 16 kg/hr of ammonia, 66 kg/hr of carbon dioxide, 10,328 kg/hr of water, 26,376 kg/hr of urea. The stream is then delivered to the first step of evaporation and subsequent process stages. The vapor-gas mixture containing 330 kg/hr of ammonia, 70 kg/hr of carbon dioxide, 4,286 kg/hr of water is fed, from the pre-evaporation separator 37, via the line 39 to the condenser 40 cooled by return water supplied via the line 41. In this condenser 40 the mixture is condensed at a temperature of 66° C. and under a residual pressure of 348 mm Hg with the formation of a liquor vapor condensate containing 264 kg/hr of ammonia, 28 kg/hr of carbon dioxide, 3,888 kg/hr of water. The liquor vapor condensate is delivered to the collector 43 via the line 42. The remaining non-condensed vapor-gas stream containing 66 kg/hr of ammonia, 42 kg/hr of carbon dioxide, 396 kg/hr of water is delivered from the condenser 40 via the line 44 to contacting, in the absorber-condenser 45, with the stream of waste waters cooled to a temperature of 37° C. in the heat-exchanger 48 and containing 6,138 kg/hr of ammonia, 1,494 kg/hr of carbon dioxide, 171,756 kg/hr of water, 612 kg/hr of urea. The stream is supplied via the line 46 by means of the pump 47 under a pressure of 1.5–2 ata. From the absorber-condenser 45 the mixed stream containing 6,204 kg/hr of ammonia, 1,636 kg/hr of carbon dioxide, 172,152 kg/hr of water, 612 kg/hr of urea and having a temperature of 40° C. is fed under a pressure close to atmospheric pressure to spraying of the absorber 50 via the line 49. This stream is intended for absorption of ammonia from the off-gases containing 512 kg/hr of ammonia, 220 kg/hr of inert gases, supplied via the line 51. From the absorber 50 the solution containing 6,536 kg/hr of ammonia, 1,536 kg/hr of carbon dioxide, water in the amount of 172,152 kg/hr, 612 kg/hr of urea and having a temperature of 42° C. is drained via the line 52 to the recycle collector 43, while the gas stream containing 180 kg/hr of ammonia, 220 kg/hr of inert gases is delivered via the line 53 to the exhaust gas collector (not shown). Also fed to the recycle collector 43 via the line 55 is a fresh condensate of the liquor vapor containing 44 kg/hr of ammonia, 66 kg/hr of carbon dioxide, 11,982 kg/hr of water, 44 kg/hr of urea; a portion of the liquid containing 442 kg/hr of ammonia, 108 kg/hr of carbon dioxide, 12,378 Kg/hr of water, 44 kg/hr of urea is withdrawn from the collector 43 via the line 54 and delivered to the system of waste water purification.

Due to the use of the process according to the present invention the rate of steam consumption is lowered by 0.05 t/t and the rate of consumption of the cooling water is lowered by 3 m$^3$/t.

EXAMPLE 4

The process is conducted under conditions similar to those described in Example 1 hereinbefore.

However, liquor vapors from the pre-evaporation unit separator containing 140 kg/hr of ammonia, 40 kg/hr of carbon dioxide, 6,140 kg/hr of water, 30 kg/hr of urea are fed via the line 56 (FIG. 3) to the condenser 57, wherein liquefaction is effected at a temperature of 64° C. under the residual pressure of 440 mm Hg to give a liquor vapor condensate containing 84 kg/hr of ammonia, 40 kg/hr of carbon dioxide, 5,766 kg/hr of water and 27 kg/hr of urea. The liquor vapor condensate is drained to a collector (not shown) via the line 58 and then treated in the unit of waste water purification. The remaining uncondensed portion of the vapor-gas mixture containing 56 kg/hr of ammonia, 374 kg/hr of water, 3 kg/hr of urea is fed via the line 59 to the absorber-condenser 60 for contacting with the recycle solution 61 containing 1,862 kg/hr of ammonia, 70,138 kg/hr of water, 24,000 kg/hr of urea having a temperature of 60° C. and supplied by a pump 62 under a pressure of 5 ata. From the absorber-condenser 60 a portion of the mixed solution containing 56 kg/hr of ammonia, 2,119 kg/hr of water, 725 kg/hr of urea is delivered via the line 64 to the second step distillation unit, while another portion of the solution containing 1,862 kg/hr of ammonia, 68,393 kg/hr of water, 23,278 kg/hr of urea remains in the circulation circuit of the absorber-condenser 60. To maintain a constant composition of the solution recycled via the line 61, to the circulation circuit there is introduced, via the line 65, a solution containing 1,744 kg/hr of water, 723 kg/hr of urea. This solution is delivered from the unit of air cleaning from urea dust.

The use of the process according to the present invention makes it possible to lower the rate of consumption of steam by 0.05 t/t and the rate of consumption of the cooling water—by 3 m$^3$/t.

EXAMPLE 5

The process is conducted under conditions similar to those of Example 1, except that the liquor vapors from the first step evaporation are passed via the line 56 (FIG. 3) to the condenser 57, wherein liquefaction is carried out at a temperature of 68° C. under a residual pressure of 230 mm Hg to give a liquor vapor condensate containing 110 kg/hr of ammonia, 40 kg/hr of carbon dioxide, 5,740 kg/hr of water, 27 kg/hr of urea.

The remaining uncondensed portion of the liquor vapors containing 30 kg/hr of ammonia, 400 kg/hr of water, 3 kg/hr of urea is delivered via the line 59 to the absorber-condenser 60 for contacting with the solution recycled via the line 61 and containing 1,008 kg/hr of ammonia, 64,272 kg/hr of water, 30,720 kg/hr of urea, having a temperature of 10° C. and supplied by means of the pump 62 under the pressure of 8 ata. From a absorber-condenser 60 a portion of the mixed stream containing 30 kg/hr of ammonia, 1,942 kg/hr of water, 928 kg/hr of urea is fed via the line 64 to the treatment in the second step distillation unit, while another portion of this stream containing 1,008 kg/hr of ammonia, 62,730 kg/hr of water, 29,795 kg/hr of urea remains in the circulation circuit of the absorber-condenser 60. The feeding stream delivered via the line 65 contains 1,542 kg/hr of water and 925 kg/hr of urea.

The process according to the present invention makes it possible to lower the rate of consumption of steam by 0.15 t/t and the rate of consumption of the cooling water—by 9 m$^3$/t.

EXAMPLE 6

The process is conducted under conditions similar to those described in Example 1 hereinbefore, except that the liquor vapors from the second step evaporation unit are passed through the condenser 57 (FIG. 3), wherein liquefaction is carried out at a temperature of 42° C. under a residual pressure of 55 mm Hg to give the liquor vapour condensate containing 134 kg/hr of ammonia, 40 kg/hr of carbon dioxide, 5,716 kg/hr of water and 28 kg/hr of urea. The remaining non-condensed portion of the liquor vapors containing 6 kg/hr of ammonia, 425 kg/hr of water, 2 kg/hr of urea is fed via the line 59 to the absorber-condenser 60 for contacting with the solution circulating via the line 61 and containing 202 kg/hr of ammonia, 57,398 kg/hr of water, 57,600 kg/hr of urea, having temperature of 20° C. and supplied by means of the pump 62 under a pressure of 10 ata. From the absorber-condenser 60 a portion of the mixed stream containing 6 kg/hr of ammonia, 1,734 kg/hr of water, 1,728 kg/hr of urea is fed via the line 64 to the treatment in the second step distillation unit. The other portion of the stream 63 containing 202 kg/hr of ammonia. 56,089 kg/hr of water, 55,874 kg/hr of urea remains in the circulation circuit of the absorber-condenser 60. The feeding stream 65 contains 1,309 kg/hr of water and 1,726 kg/hr of urea.

The use of the process according to the present invention makes it possible to lower the steam consumption rate by 0.07 t/t and the rate of consumption of the cooling water—by 4.5 m$^3$/t.

What is claimed is:

1. A process for producing urea comprising:
   (a) synthesis of urea from ammonia and carbon dioxide under a pressure of from 140 to 400 ata at a temperature of from 160° to 230° C.;
   (b) separation of the resulting aqueous solution of urea from the ammonia and carbon dioxide not converted to the desired product;
   (c) separation of liquid or gaseous streams of ammonia and carbon dioxide from gases inert to the synthesis of urea and from the purified waste water withdrawn from the process;
   (d) recycling said liquid or gaseous streams of ammonia and carbon dioxide to the synthesis of the desired product;
   (e) vacuum thickening the resulting solution of urea under a pressure of from 0.04 to 0.90 ata with the recovery of dehydrated urea in the condensed phase, and a vapor phase consisting of a mixture of water, ammonia, carbon dioxide and urea;
   (f) converting the dehydrated urea into solid particles and cooling in a stream of air;
   (g) water washing urea dust from the air from the stage of converting the dehydrated urea into solid particles and cooling with the formation of an aqueous solution of urea delivered to said stage of vacuum thickening;
   (h) condensation of the mixture of water, ammonia, carbon dioxide and urea from the vapor phase from the stage of vacuum thickening due to its indirect cooling with the formation of a liquor vapor condensate;
   (i) supplying the liquor vapor condensate to the stage of separation of the gases inert to the synthesis of urea and purified waste water;
   (j) supplying the ammonia and carbon dioxide contained in the uncondensed portion of the vapor phase from the stage of vacuum thickening after said indirect cooling to the stage of separation of the gases inert with respect to the synthesis of urea and purified waste water; wherein the uncondensed portion of the vapor phase from the stage of vacuum thickening after said indirect cooling is subjected to absorption-condensation under a pressure at which said vapor phase is fed to the stage of absorption-condensation, said absorption-condensation being carried out by means of direct contact of said vapor phase with a cooling agent-absorbent having a temperature of from 10° to 60° C. and a pressure of from 1.5 to 18 ata and containing dissolved in water 0.2 to 3.4% by weight of ammonia, 0 to 1.0% by weight of carbon dioxide and 0 to 50% by weight of urea, whereafter at least a portion of the resulting solution is passed to the stage of separation of the gases inert to the synthesis of urea and purified waste water, or to the stage of separation of the aqueous solution of urea from the ammonia and carbon dioxide not converted to the desired product, or to the stage of vacuum thickening of the solution of urea.

2. A process as claimed in claim 1, wherein the absorption-condensation is carried out using the liquor vapor condensate as the cooling agent-absorbent.

3. A process as claimed in claim 1, wherein as the cooling agent-absorbent use is made of the waste waters purified from the contaminating urea under a pressure of from 16 to 18 ata at the stage of separation of the gases inert to the synthesis of urea, and waste purified waste water.

4. A process as claimed in claim 1, wherein as the cooling agent-absorbent use is made of the solution of urea resulting from water washing of urea dust from the air from the stage of converting of the dehydrated urea into solid particles and their cooling and/or the solution of urea resulting from the separation of the aqueous solution of urea from the ammonia and carbon dioxide not converted to the desired product.

* * * * *